(12) United States Patent
Giniger

(10) Patent No.: US 8,580,232 B2
(45) Date of Patent: Nov. 12, 2013

(54) COMPOSITIONS FOR ENHANCING EFFECTS OF OTHER ORAL CARE COMPOSITIONS

(76) Inventor: Martin S. Giniger, Pompano Beach, FL (US)

( * ) Notice: Subject to any disclaimer, the term of this patent is extended or adjusted under 35 U.S.C. 154(b) by 0 days.

(21) Appl. No.: 12/970,836

(22) Filed: Dec. 16, 2010

(65) Prior Publication Data

US 2011/0085991 A1  Apr. 14, 2011

Related U.S. Application Data

(62) Division of application No. 11/356,445, filed on Feb. 15, 2006, now abandoned.

(60) Provisional application No. 60/653,421, filed on Feb. 15, 2005, provisional application No. 60/734,549, filed on Nov. 7, 2005, provisional application No. 60/734,477, filed on Nov. 7, 2005.

(51) Int. Cl.
| | |
|---|---|
| *A61K 8/365* | (2006.01) |
| *A61K 8/00* | (2006.01) |
| *A61K 8/49* | (2006.01) |
| *A61K 8/21* | (2006.01) |
| *A61K 8/97* | (2006.01) |
| *A61K 8/46* | (2006.01) |
| *A61K 8/42* | (2006.01) |
| *A61K 8/22* | (2006.01) |
| *A61Q 11/00* | (2006.01) |

(52) U.S. Cl.
USPC .................. 424/52; 424/49; 424/53; 424/54; 424/56; 424/58

(58) Field of Classification Search
USPC ....................................... 424/49, 53
See application file for complete search history.

(56) References Cited

U.S. PATENT DOCUMENTS

| 5,928,628 A * | 7/1999 | Pellico ............................ 424/49 |
| 2005/0118115 A1* | 6/2005 | Fontenot ......................... 424/53 |

* cited by examiner

*Primary Examiner* — Walter Webb
(74) *Attorney, Agent, or Firm* — Scull, Peter Hamilton DeSanctis & Cha, LLP

(57) ABSTRACT

An enhancing composition comprising a solvent and a base compound creates an alkaline environment for activating peroxide whiteners and accelerating the formation of free radicals from the peroxide to effect the oxidation of organic molecules causing staining of the dentition. In one embodiment, potassium hydroxide is dissolved in water to form a strongly alkaline liquid. A surfactant may also be included to clean the surfaces of the user's teeth in advance of application of the whitening composition. A peroxide may be added to the enhancing composition to provide a tooth whitening. Other additives for taste, texture, viscosity, and other oral care or oral hygiene purposes may also be included in the enhancing composition. The enhancing composition may be used for advance application to the dentition before a whitening compound. In addition, a rinse may be used after the whitening composition to neutralize the alkaline environment.

4 Claims, 2 Drawing Sheets

COMPOSITIONS FOR ENHANCING EFFECTS OF OTHER ORAL CARE COMPOSITIONS

CROSS-REFERENCE TO RELATED APPLICATIONS

The present invention is a divisional of U.S. patent application Ser. No. 11/356,445, filed on Feb. 15, 2006, which claims the benefit of and priority from the prior-filed U.S. Provisional Patent Applications, No. 60/653,421; filed Feb. 15, 2005, entitled "Whitening System Capable of Delivering Effective Whitening Action"; and No. 60/734,549; filed Nov. 7, 2005, entitled "Oral Care Compositions and Methods"; and No. 60/734,477 filed Nov. 7,2005, entitled "Compositions for Enhancing the Effects of Other Oral Care Compositions"; the subject matter of each of which hereby being specifically incorporated herein by reference for all that they disclose and teach.

BACKGROUND

The present invention relates to improvements in oral care compositions, and more particularly relates to a composition for enhancing the effects of tooth whitening compositions.

In the state of the art of oral care compositions and the delivery of such compositions to the site of use in the oral cavity, many means and methods have been utilized and yet numerous issues remain. For an effective ingredient of an oral care composition to have a therapeutic effect, whether for oral cleaning, treatment, or tooth whitening, the effective ingredient must reach and maintain effective contact with the oral care feature long enough to provide its intended effect. Thus, dispersion and penetration into and between the surfaces of various oral features such as the odd shapes of the nooks and crannies of adjacent teeth is a continual issue. So too then is the dwell or contact time necessary or at least preferred for having the effective ingredient or ingredients of an oral care composition maintained in contact with or otherwise disposed adjacent the surface of the oral feature being eared for. Such issues arise in various oral cleaning, treatment and/or tooth whitening situations.

In tooth cleaning and/or treatment, effective ingredients such as fluoride or an anti-gingival agent, e.g., triclosan, must reach the areas between teeth or between a tooth and gums and/or reach the nooks and crannies on/of teeth to provide their benefits to those oral features. Similar activities are necessary in tooth whitening as well. In considering tooth whitening generally, it may first be noted that a tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person ingests on a daily basis can "stain" or reduce the "whiteness" of one's teeth. In particular, foods, tobacco products, and fluids such as tea and coffee that one consumes tend to stain one's teeth. These products or substances tend to accumulate on the enamel layer of the teeth and form a pellicle film on the teeth. These staining and discoloring substances can then permeate the enamel layer. This problem occurs gradually over many years, but imparts a noticeable discoloration of the enamel of one's teeth.

Many different oral compositions for stain removal or tooth whitening are available to consumers and dentists for home and professional in-office use. Many of these compositions contain 1-45% by weight concentrations of a peroxygen compound such as hydrogen peroxide and, when applied on the teeth, may effect whitening of stains. These compositions all require different amounts of time to achieve a desired tooth bleaching effect. These times range from 90 to 120 minutes for a dentist-applied, light-activated bleaching system to two weeks or more of overnight exposure for consumer-applied, tray-delivered whitening products. Currently, even the top selling brands of dentist-applied, light-activated, chair-side tooth whitening systems require a minimum of three (3) twenty-minute applications and an overall minimum of ninety (90) minutes or more to complete when all manufacturers' instructions are followed, Among the chemical strategies available for removing or bleaching tooth stains, the most effective compositions contain an oxidizing agent, usually a peroxygen compound such as hydrogen peroxide, in order to attack the chromogen molecules forming the stains in such a way as to render them colorless, water-soluble, or both. In one of the most popular approaches to whitening a patient's teeth, a dental professional will construct a custom-made, tooth-bleaching tray for the patient from an impression made of the patient's dentition. A prescription oxidizing gel is dispensed into the room-bleaching tray and worn intermittently over a period of time ranging from about 2 weeks to about 6 months, depending upon the severity of tooth staining. These oxidizing compositions, usually packaged in small plastic syringes are dispensed directly by the patient into the custom-made, tooth-bleaching tray and are held in place in the mouth for typical contact times of greater than about 60 minutes, and sometimes as long as 8 to 12 hours. The slow rate of bleaching is in large part due to the nature of the formulations developed to maintain stability of the oxidizing composition.

Alternatively, some oxidizing compositions with relatively high concentrations of oxidizers are applied directly to the tooth surface of a patient in a dental office setting under the supervision of a dentist or dental hygienist. Supervision of application is required with the high concentration oxidizers because of the potential for damage to gums and other oral tissue from the misapplication of highly concentrated oxidizers. Theoretically, such tooth whitening strategies have the advantage of yielding faster results and better overall patient satisfaction.

Oral compositions for whitening teeth are also available containing peracetic acid dissolved or suspended in a vehicle. The peracetic acid may be generated within a dentifrice vehicle by combining water, acetylsalicylic acid, and a water soluble alkali metal percarbonate. Formulatsons for oxygen liberating compositions for the whitening of teeth also use either anhydrous and/or hydrated pastes or gels. Hydrated examples include an aqueous oral gel composition comprising about 0.5% to about 10% by weight urea peroxide and 0.01% to 2% by weight of a fluoride compound, and/or a water containing a hydrogen peroxide-Pluronic thickened oral gel composition. Other examples of whitening or stain removal compounds include toothpastes containing a combination of calcium peroxide and sodium perborate oxidising agents, dicalcium phosphate, calcium carbonate and magnesium carbonate cleaning agents, sorbitol humectant, cornstarch and cellulose gum thickening agents, and an anionic detergent. Oral compositions containing peroxyacids and alkyl diperoxy acids having alkylene groups containing 5-11 carbon atoms are also used for removing stains from teeth.

Another conventional whitening technique is the administration of a light-activated gel under the supervision of a dentist using a protocol of a usual three (3) twenty minute applications. However, patients frequently become uncomfortable, agitated, and/or bored during such a procedure, which typically lasts between 1½ to 2 hours when all set-up and precautionary methods are included. Also, because of the length of exposure to both the gel and the light, teeth and oral tissues can become irritated or experience a transient hypersensitivity reaction. Thus, any improvement that results in decreased exposure time, increased patient comfort and increase in bleaching efficiency is desirable.

In one variation, light or photo-activation implementations have also been developed for use alone or in incorporation with the peroxygen compounds. Here, many kinds of ultraviolet (UV) photo-activators have been identified that naturally reduce the color of chromophoric stains. Exemplary photo-activators include transition metal complexes, keto acids, riboflavin, pteridines, algal pigments, cyanocobalamine, thiamin, biotin, and aromatic ketones. Photo-beaching of tooth surfaces theoretically occurs via one of two pathways. First, the substrate may undergo photoreaction directly if the absorption spectrum of the colored chromagen overlaps with the spectrum of incoming radiation (i.e., the color of the stain fades with exposure to light). Second, UV energy may be absorbed by photo-activators that then chemically react with tooth surface chromagens resulting in an "indirect" photo-bleaching. This is likely a more powerful means for effecting color changes. Indirect photo-bleaching may be mediated by transient species (free radicals) that are rapidly consumed by subsequent reactions. For these mechanisms, the rate of reaction is determined by the quantities and types of chromagens, activators, free radicals, and incoming UV radiation. Surface gradients involving any of these factors will lead to altered rates of photo-bleaching at the enamel/bleaching agent interface.

In nature, the major photochemical intermediate free radicals include singlet oxygen ($IO_2$); superoxide ($O_2$—), hydroperoxide ($HO_2$), and various other peroxy radicals, ($RO_2$). These have been described in a large number of publications including a number of patents for the purpose of bleaching teeth. Singlet oxygen free radicals, $1O_2$ (the most common type of free radical liberated from hydrogen peroxide ($H_2O_2$) in the presence of light, heat, or most activators), are formed primarily through energy transfer from the excited triplet states of dioxygen, $3O_2$ (as seen in the case of hydrogen peroxide). Wavelengths in the UV-A (315-400 nm) and UV-B (280-315 nm) ranges have been shown to be most effective in their formation. Quantum yields (i.e., the fraction or percentage of absorbed photons which give rise to these free radical products) range from 1% to 3% and generally decrease with increasing wavelength. Because the high concentrations of $H_2O_2$ or similar compounds are present in tooth bleaching preparations, the decay of $H_2O_2$ into water and $1O_2$ is prominent when UV light/activator systems are used in professional tooth bleaching formulas.

The exact mechanism of how these singlet oxygen free radicals come to be formed still remains unclear. Some researchers have suggested that $1O_2$ is formed by direct electron transfer from the excited triplet states to $O_2$. However, reduction of $O_2$ by radicals or radical ions produced by intramolecular electron transfer reactions, H-atom abstractions and/or hemolytic bond cleavages is equally, if not more, plausible. However, it is known that transition metal complexes having single electron reduction potentials falling between the $O_2/O_2$— and $O_2$—/$H_2O_2$ couples can rapidly catalyze $1O_2$ free radical formation.

A commercial application has been made of oxidation from the photo-fenton reaction in which reduced metals such as Fe(II) react with $H_2O_2$ and UV light to produce a single OH— radical. This may be because hydroxyl moieties may be generated with less UV activation energy reduction in a chromophoric tooth stain in a given period of time or for a given level of UV energy (the high quantum yield for this reaction is 98%).

These extant methods are not quickly or highly effective and indeed need prolonged periods for any minimum effective bleaching effects. These time-consuming methods for teeth whitening thus suggest that any whitening system that can reduce the time factor is desirable.

SUMMARY

An activation or enhancing composition creates an alkaline environment for activating peroxide whiteners and accelerating the formation of free radicals from the peroxide to effect the oxidation of organic molecules causing staining of the dentition. The activation or enhancing composition hereof may be used for advance application to the dentition before the application of any whitening compound. The primary components of such an enhancing composition hereof are a solvent and a base compound. An exemplary solvent is water. One exemplary base that may be used is potassium hydroxide (KOH), which easily dissolves in water to form a strongly alkaline liquid. The dissolution of KOH in water also generates substantial heat, which may be conducive to the dissolution of additional ingredients in the enhancing composition. Other basic compounds may alternatively be used to create the alkalinity of the enhancing composition. A surfactant may also be included to clean the surfaces of the user's teeth In advance of application of the whitening composition. A peroxide may be added to the enhancing composition to provide tooth whitening. Other additives for taste, texture, viscosity, and other oral care or oral hygiene purposes may also be included in the enhancing composition.

The enhancing composition may be used as part of a tooth whitening process to enhance the effect of a whitening composition. The enhancing composition is generally applied to a user's dentition in advance of a whitening or bleaching composition. In addition, a rinse may be used after the application of the whitening composition to neutralize the alkaline environment in the oral cavity caused by the enhancing composition and return the user's mouth to a neutral pH.

DETAILED DESCRIPTION

Figure 1:
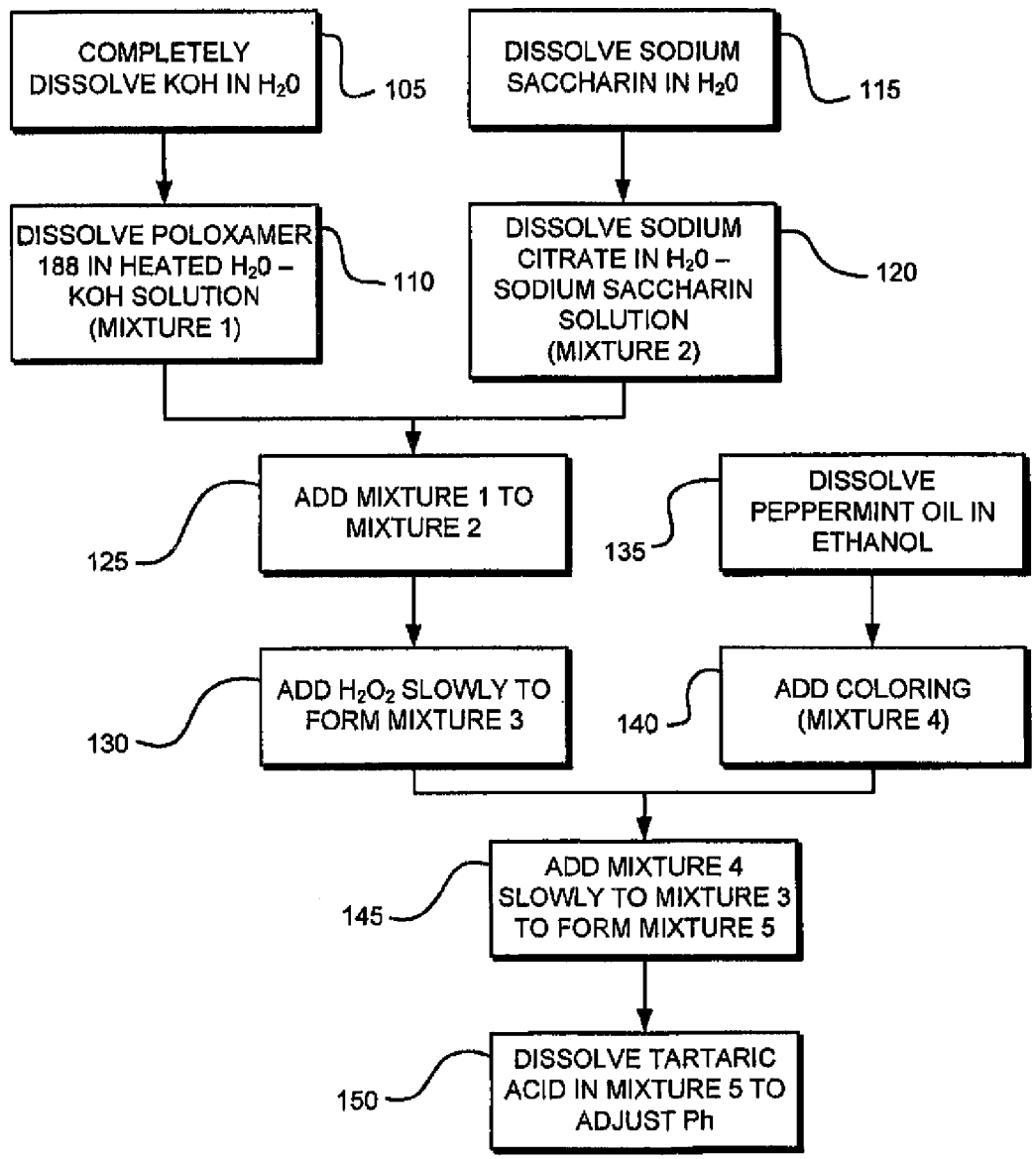
FIG. 1 is a flow diagram of an exemplary series of steps for creating an enhancing composition.

The detailed description set forth herein is intended as a description of several exemplary compositions for enhancing the effectiveness of tooth whitening and/or other oral care compounds according to the present invention and is not intended to represent the only forms in which such compositions may he prepared or utilized. The description sets forth features of and steps for preparing and using the enhancer compositions of the present invention. It is to be understood, however, that the same or equivalent ingredients incorporated in different embodiments of enhancer compositions may accomplish the same functions or achieve the same results and such compositions are also intended to be encompassed within the spirit and scope of this description.

Many oral care compositions, for example, tooth whitening compositions include at least one peroxide compound to create a tooth whitening composition. The peroxide may be hydrogen peroxide ($H_2O_2$) or it may be one or more of other peroxides, for example, metal-ion-free peroxide compounds including urea peroxide (carbamide peroxide), salts of peroxides formed from the alkali and alkaline earth metals (e.g., calcium peroxide), glyceryl peroxide, benzoyl peroxide, and other organic peroxides. The peroxide may be a mixture of peroxides, for example, hydrogen peroxide and carbamide peroxide, or calcium peroxide with either or both hydrogen peroxide and carbamide peroxide.

Organic molecules, for example, chromagens, are often involved in the stains in discolored teeth. Carbon double bonds in organic molecules act as pigments. Chemically, peroxides give up a free radical oxygen atom when activated by an appropriate light source or chemical compound. Once released in the vicinity of teeth, the free radical oxygen atom attacks the carbon-carbon bonding structure of the organic molecule producing the stain. The offending molecule is oxidized and die oxygen is reduced. When there is an excess of hydroxy anion ($OH^-$) present, the proton ($H^+$) ion is abstracted from the peroxide. Once the peroxide is missing the proton that it gave to the hydroxy ion, the peroxide molecule must give up a free radical oxygen. Thus, the reaction allowing release of stain-removing oxygen can be driven chemically.

The amount of whitening obtained during tooth bleaching with peroxide compositions is generally dependent upon: (1) the length of time the teeth are in contact with the whitening agent; (2) the number and/or length of periods (e.g., hours and/or days) the treatment is carried out; (3) the susceptibility of the teeth to the bleaching agent; and (4) the concentration of active peroxide. For maximum whitening, a long treatment time with a highly concentrated bleaching composition has generally been recommended.

Chemical reactions are often affected by the relative acidity or alkalinity of the solution or environment in which the reaction occurs. Acidity and alkalinity are measured in terms of the relative presence or absence of hydrogen ions ($H^+$), which was originally termed the "power of Hydrogen" or "pH." The measure of pH is indicated as a number on a logarithmic scale, wherein a value of 7 represents neutrality, lower numbers-indicate increasing acidity, and higher numbers indicate increasing alkalinity. Each unit of change on the pH scale is the negative logarithm of the effective hydrogen ion concentration or hydrogen ion activity in gram equivalents per liter of the solution and thus represents a tenfold change in acidity or alkalinity.

The liberation of free radical oxygen from a peroxide to effect stain removal can be performed by increasing the energy level of the peroxide molecule by adding energy to it or by chemically pushing the peroxide solution to a basic pH number. However, hydrogen peroxide in most tooth whitening compounds is generally carried in a slightly acidic solution in order to stabilize the peroxide before application. Thus, the normal application of a standard hydrogen peroxide whitening compound does not occur in a favorable reaction environment. Contrarily, an effective, biologically compatible environment for bleaching with hydrogen peroxide is at a slightly basic pH of between approximately 8.5 and 9.5, with a pH of about 8.8 being optimal. Biologic compatibility refers to a pH level that, while providing a catalytic benefit to the peroxide bleaching reaction, does not cause damage to oral tissues surrounding the dentition.

The present invention is directed to creating this alkaline environment for activating peroxide or other whiteners and accelerating the formation of free radicals from the peroxide to effect the oxidation of organic molecules causing staining of the dentition. In one embodiment, an enhancing composition is provided for advance application to the dentition before the application of any whitening compound. The primary components of such an enhancing composition may be water, which functions primarily as a carrier or solvent, and a base compound. One exemplary base that may be used is potassium hydroxide (KOH), which easily dissolves in water with much heat to form a strongly alkaline liquid. The dissolution of KOH in water typically also generates substantial heat, which may be conducive to the dissolution of additional ingredients in the enhancing composition. Other basic, compounds may alternatively be used to create the alkalinity of the enhancing composition.

Enhancing compositions according to the present invention may further include a surfactant. Suitable surfactants may be anionic, nonionic, amphoteric, Kwitterionic, cationic, and mixtures thereof. Anionic surfactants include, but are not limited to water-soluble salts of alkyl sulfates having from 8 to 20 carbon atoms in the alkyl radical (e.g., sodium alkyl sulfate), water-soluble salts of sulfonated monoglycerides of fatty acids having from 8 to 20 carbon atoms, and mixtures thereof. Examples of anionic surfactants include sodium lauryl sulfate, sodium coconut monoglyceride sulfonates, phospholipids, sareosinates such as sodium lauryl sarcosinate, taurates, sodium lauryl sulfoacetate, sodium lauroyl isethionate, sodium laureth carboxylate, and sodium dodecyl benzenesulfonate. Many of these anionic surfactants are disclosed in U.S. Pat. No. 3,959,458, which is hereby incorporated herein by reference in its entirety.

Nonionic surfactants may Include, but are not limited to, compounds comprising hydrophilic (having an affinity for water) and hydrophobic components (lacking an affinity for water). These surfactants may be produced by the condensation of alkylene oxide groups, which are hydrophilic in nature, with an organic hydrophobic compound, which may be aliphatic or alkyl-aromatic in nature. Examples of suitable nonionic surfactants include low viscosity poloxamers, e.g., poloxamer 188 (under trade name Pluronic), low viscosity hydroxyethyl cellulose, polysorbates, polyoxyethylene sorbitan esters (under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures thereof.

Amphoteric surfactants may include, but are not limited to, derivatives of aliphatic secondary and tertiary amines in which the aliphatic component may be a straight chain or branched. One of the aliphatic substituents may contain from about 8 to about 18 carbon atoms and one may contain an anionic water-solubilizing group, e.g., carboxylate, sulfonate, sulfate, phosphate, phosphonate, betaines (e.g., cocamidopropyl betaine), and mixtures thereof. Many of these nonionic and amphoteric surfactants are disclosed in U.S. Pat. No. 4,051,234, which is hereby incorporated herein by reference in its entirety.

Any asymmetrical molecule dissolved in water will make at least a weak surfactant. Such weak surfactants may not normally be effective foaming agents, but the effectiveness can be improved if an alternatively available foaming dispenser is used. Asymmetrical molecules as contemplated herein may include those that contain a hydrophilic and a hydrophobic segment. One end of the molecule is thus polar in nature and dissolves in water, while the other end is non-polar in nature, avoids water, and dissolves in oil and other nonpolar compounds. When in water, their polar ends of these surfactant molecules are oriented toward the water molecules, while the non-polar ends attract non-polar molecules. The non-polar ends of the surfactant molecules lift stain molecules from the tooth surface by loosening the molecules, breaking them up, and holding them onto the asymmetric molecules, allowing them to be washed away with the water.

Surfactants may also be included in the oral care enhancing compositions in solid form. Solid form surfactants may include, for example, sodium carbonate anhydrous, sodium bicarbonate, potassium iodide, and mixtures thereof. Exemplary surfactants may also include at least some difunctional block copolymer surfactants, e.g., those having terminal groups of primary hydroxyl groups, and groups comprising a hydrophobic and a hydrophilic segment. Examples include Pluronic F68, Pluronic F88, and mixtures thereof. The amount of a surfactant used in an oral care enhancing composition may be in a range approximated by the amount given In the below example, TABLE 1.

The enhancing composition may further include ingredients for affecting the taste and feel of the enhancing composition by a user. For example, flavor oils such as peppermint oil or cinnamon oil may be included to provide a pleasing flavor to the enhancing composition. Sodium saccharin, sucralose, aspartame, or other sweetening agents may be used to enhance the flavor. Sodium citrate may be added as an anticoagulant to improve the feel of the enhancing composition in the mouth. It may also enhance the effectiveness of any surfactant by preventing interference from any calcium ions present.

The enhancing composition may further include a peroxide or a salt of chlorous acid as used in the whitening compound, as for example but not limited to, hydrogen peroxide. Other peroxygen containing or generating compounds may also be used herewith. In many examples, for increasing peroxide stability during storage, a 3% di-sodium EDTA may be added to the enhancing composition. Alternatively, stability may be enhanced by refrigeration or otherwise storing the product in a dark, cool, dry place.

The composition of the present invention can also include other active ingredients, such as peroxide photo-activators. The addition of peroxide photo-activators can also increase the photobleaching efficiency of the foamable compositions of the present invention. Suitable peroxide photo-activators include those with lower oxidative state transition metal salt. The metal salt may catalyze the bleaching action of the peroxide to produce faster effective bleaching at lower peroxide concentrations. The preferred transition metals are those of lower atomic numbers including lower atomic number transition metals such as those ranging from atomic number 21 to 30. Also, those with lower oxidative states may be more preferred, including, e.g., Iron(II), manganese(II), cobalt(II), copper(II) and mixtures thereof, and most preferably Iron(II), as in a ferrous gluconate. When used, only a very small amount of the transition metal salt is needed, for example, from about 0.01% by weight to about 4% by weight, further for example, from about 0.03% by weight to about 2% by weight, and even further for example, from about 0.04% to about 1% by weight. The peroxide photo-activator can also include alkali salts such as potassium iodide, potassium chloride, sodium iodine, sodium chloride and combinations thereof.

Amorphous calcium compounds such as amorphous calcium phosphate (ACP), amorphous calcium phosphate fluoride (ACPF) and amorphous calcium carbonate phosphate (ACCP) amorphous calcium carbonate phosphate (ACCP), and amorphous calcium carbonate phosphate fluoride (ACCPF) can be used in re-mineralizing teeth. These amorphous compounds are disclosed in U.S. Pat. Nos. 5,037,639, 5,268,167, 5,437,857, 5,562,895, 6,000,341, and 6,056,930, the disclosure of each of which hereby being incorporated by reference in its entirety.

In addition to or as an alternative to amorphous calcium compounds, amorphous strontium compounds such as amorphous strontium phosphate (ASP), amorphous strontium phosphate fluoride (ASPF), amorphous strontium calcium phosphate (ASCP), amorphous strontium calcium carbonate phosphate (ASCCP), amorphous strontium carbonate phosphate fluoride (ASCPF) and amorphous strontium calcium carbonate phosphate fluoride (ASCCPF) may be included for use in re-mineralization, as noted above. Such compounds are disclosed in U.S. Pat. No. 5,534,244, the content of which hereby incorporated by reference in its entirety.

For example, the whitening compound may include a source of phosphate and the second component may include a source of calcium or strontium. For example, the source of phosphate in the first component includes monosodium phosphate ($NAH_2PO_4$), disodium phosphates tetrapotassium pyrophosphate and relatives thereof. As introduced above, the whitening component may include a source of calcium or strontium, which combines with phosphate to form the various amorphous calcium and/or strontium phosphates. The source of phosphate may be, for example, present in an amount of from about 0.2% to about 5% by weight. The source of calcium, strontium, or combinations thereof may include a calcium salt, a strontium salt, and thereof, further for example, a calcium salt such as calcium nitrate, in an amount of from about 0.25% by weight to about 1.5% by weight. The source of phosphate and the source of calcium, strontium or mixture can combine to form calcium phosphate. When applied to the teeth, the calcium phosphate can precipitate onto the surface of the teeth where it may be incorporated into hydroxyapatite, assisting in remineralization of the tooth enamel, as discussed in U.S. Pat. Nos. 5,037,639; 5,268,167; 5,460,803; 5,534,244; 5,562,895; 6,000,341; and 6,056,930 noted above.

In practice, it may in some embodiments be preferred to include as much phosphate as possible, as the phosphate salt further acts to adjust the pH of the first component. The pH of the system is from, for example, about 5 to about 8, or for a further example, from about 5.5 to about 6.5.

Note also, the fluoride-containing amorphous compounds described here may also be used in fluoridating teeth. Otherwise, as mentioned, fluorides may be added separately and then, many, if not all of the above amorphous compounds or solutions which form the amorphous compounds, when applied either onto or into dental tissue, particularly in the presence of fluoride, may operate to promote fluoridation. Such fluoridation or other mineralization may serve to assist in prevention and/or repair of dental weaknesses such as dental caries, exposed roots and dentin sensitivity.

The enhancing composition of the present invention can also include other active ingredients, such as de-sensitizing agents and/or antimicrobial or antibacterial agents. Even with improved efficiency and shorter treatment time, some patients may still experience sensitivity from tooth whitening compositions. Inclusion of desensitising agents in the enhancing composition allows time for desensitization of the oral tissue before the application of the whitening compound. Suitable desensitising agents can include Eugenol and/or alkali nitrates such as potassium nitrate, sodium nitrate, and lithium nitrate and other potassium sails such as potassium chloride and potassium bicarbonate. The desensitising agent may make up to about 3% to 5% percent by weight of the enhancing composition. Eugenol may also act as an antimicrobial or antibacterial agent.

Further additives may include calcium nitrate and/or sodium mono and/or dibasic hydrate. These compounds may be added to lower the viscosity of the enhancing composition and provide a composition that has greater ability to penetrate recesses and interstices of the dentition. Such additives may also improve the stability of the enhancing composition. Potassium nitrate may alternatively and/or additionally be added to achieve desired viscosity effects.

In addition, optional additives including emulsifiers, flavorings, coloring agents, anti-plaque agents, anti-staining compounds, excipients such as emollients, preservatives, other types of stabilizers such as antioxidants, chelating agents, tonicity modifiers (e.g., sodium chloride, manitol, sorbitol, or glucose), spreading agents, pH adjusting agents and water soluble lubricants, e.g., propylene glycol, glycerol, or polyethylene glycol may be included in the enhancing composition. The concentration of each may easily be determined by a person skilled in the art. Lecithin, a natural emulsifier found in soy and other plants, and gum arabic, which comes from the sap of certain species of acacia trees, can be added for use as an emulsifier, dispersant, and/or wetting agent. Suitable preservatives may include benzalkonium chloride, parabens, chlorhexidine acetate, chlorhexidine gluconate, sorbic acid, potassium sorbitol, chlorbutanol, and phenoxyethanol. Suitable emollients such as those used for topical applications are, for example, di-n-octyl ether, fatty alcohol polyalkylene glycol ether, 2-ethylhexyl palmitate, and isopropyl fatty acid esters.

An exemplary formula for an enhancing composition according to the present invention is presented in Table 1 below. Water is used as the primary carrier and solvent for the remaining ingredients. Potassium hydroxide is incorporated as the peroxide activator and pH modifier. Other optional ingredients which may provide certain functionalities may include tartaric acid to adjust the final pH of the enhancing composition to a biologically compatible level and hydrogen peroxide to initiate the whitening process. Several non-active ingredients include Pluronic F68 as a gelling agent, sodium laurel sulfate as a stain remover, sodium saccharin as a sweetener, sodium citrate for improved oral sensation, peppermint oil for flavor and scent, ethanol as an antibacterial agent, and a color additive for visual interest.

TABLE 1

| Ingredient | Amount | Chemical/ IUPAC "real name" | Source | Purpose |
|---|---|---|---|---|
| water ($H_2O$) | 80 ml | | N/A | carrier/solvent |
| potassium hydroxide (KOH) | 0.1 g | Same | Spectrum Chemical | peroxide activator/pH modifier |
| Pluronic F68 | 0.5 g | poloxamer 188 | BASF | gelling agent |
| sodium laurel sulfate (SLS) | 0.5 g | Same | | stain remover |
| sodium saccharin | 0.3 g | Same | | sweetener |
| sodium citrate ($Na_3C_6H_5O_7$) | 0.7 g | Same | | oral sensation |
| Hydrogen peroxide ($H_2O_2$) (30%) | 6.7 g | Same | Autofina | bleaching agent |
| peppermint oil | 0.3 g | Same | S&S Flavors | flavor, scent, stabilizer |
| ethanol ($C_2H_5OH$) | 8.6 g | Same | Spectrum Chemical | anti-bacterial |
| red color | 2 drops | Same | Warner Jenkins | colorant |
| tartaric acid ($C_4H_6O_6$) | 0.1 g | Same | Spectrum Chemical | pH modifier |

The ingredients of Table 1 including the exemplary enhancing composition may be mixed according to the exemplary method depicted in FIG. 1. Initially, approximately 0.1 g of potassium hydroxide is completely dissolved in 60 ml of water (step 105). The dissolution of potassium hydroxide is an exothermic process that heats the solution. Next, approximately 0.5 g of poloxamer 188 is dissolved in the $H_2O$—KOH mixture (step 110). The generation of heat is advantageous because heat may be beneficial for the dissolution of the poloxamer 188. Application of additional heat to the mixture may assist in completely dissolving the poloxamer 188. The mixture of $H_2O$, KOH, and poloxamer 188, which may be referred to as Mixture 1, is set aside.

A second mixture, Mixture 2, is prepared by dissolving approximately 0.3 g of sodium saccharin in 20 ml of water (step 115). Mixture 2 is completed by dissolving approximately 0.7 g of sodium citrate into the water-sodium saccharin solution (step 120). Mixture 1 is men combined with Mixture 2 (step 125). Next, approximately 6.7 g of 30% hydrogen peroxide solution is slowly introduced to the combination of Mixture 3 and Mixture 2 to form Mixture 3 (step 130). Mixture 3 may then be set aside.

Another mixture, Mixture 4, is created by dissolving approximately 0.3 g of peppermint oil in approximately 8.6 g of ethanol (step 135). Several drops of a coloring additive, for example, food coloring, may be added to Mixture 4 to provide visual interest to the enhancing composition (step 140). In the ingredients depicted in Table 1, approximately two drops of red coloring may be added to Mixture 4.

Next, Mixture 4 is slowly added to Mixture 3 to form Mixture 5 (step 145). Finally, approximately 0.1 g of tartaric acid may be added to Mixture 5 (step 150) to adjust the basic pH of Mixture 5 downward to a biologically compatible level, for example, between about 8.5 and 9.5, with a target pH of about 8.8. The mixture of the ingredients in Table 1 according to the steps set forth in FIG. 1 thus results in a 100 ml volume of an exemplary enhancing composition for pretreatment of dentition before application of a tooth whitening composition. The increase in pH created by the enhancing composition enhances the effectiveness of the tooth whitening compound.

Although certain steps for combining the ingredients identified in Table 1 are indicated in FIG. 1 and the accompanying discussion above, it should be recognized that additional or alternative ingredients described above may also be included or substituted in the enhancing composition. Further, the steps depicted in FIG. 1 are merely exemplary and other variations for mixing ingredients of the enhancing composition are possible and contemplated.

The enhancing composition may be applied to a user's dentition in any of a variety of ways. For example, if the enhancing composition has a low viscosity, the enhancing composition may be provided in the form of a mouth rinse. At a higher viscosity, for example, in the form of a gel or paste, the enhancing composition may be applied with a brush or a swab. The enhancing composition may be in the form of a tooth paste and applied with a standard tooth brush. The enhancing composition may also be applied with a brush more closely resembling a paint brush. If the enhancing composition is applied with a swab (e.g., the enhancing composition is a gel), the swab may be formed of a foam material rather than other materials. Foam is more structurally sound and uniformly absorptive as compared to cotton swabs or other materials. Foam also is resistant to breaking down and does not permanently deform.

In addition to the enhancing composition, a post-whitening rinse composition may also be used as part of a complete tooth whitening process. The primary purpose of the post-whitening rinse compound is to return the pH within the user's mouth after a bleaching application to neutral. An exemplary bleaching composition is described in copending U.S. patent application Ser. No. 11/356,468, entitled "Oral care cleaning compositions and methods," filed Feb. 15, 2006, which is hereby incorporated herein by reference. Any other commercially available bleaching or whitening composition may likewise be used in conjunction with the enhancing composition and rinse composition. An exemplary rinse composition maybe slightly acidic, for example, about 5,5 pH, to reduce the pH from the more basic level of between 8.5 and 9.5 created by the enhancing composition to neutral pH of about 7.

Figure 2:
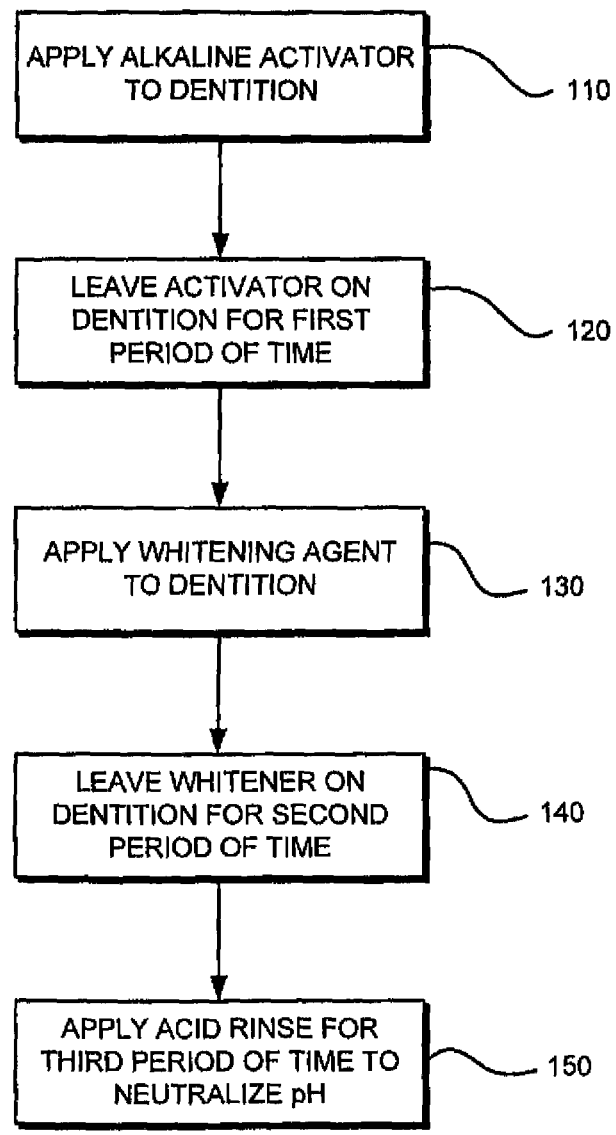
FIG. 2 is a flow diagram of an exemplary series of steps for applying the enhancing composition as part of a tooth whitening process.

FIG. 2 depicts an exemplary tooth whitening process including steps of enhancing, whitening, and rinsing. First, an alkaline enhancing composition according to the description herein is applied to a user's dentition (step 210). As indicated above, application of the enhancing composition may be by rinse, swab, or brush. The enhancing composition is left on the user's dentition for a first period of time (step 220). For example, if tire enhancing composition is for over-the-counter consumer use, the application period may be on the order of about a second up to approximately a few minutes. Alternatively, if the enhancing composition is of a greater pH than a consumer composition and is applied by a dental practitioner In a clinical setting, the application period may be of an even shorter period of time.

Once the enhancing period expires, a whitening composition may then be applied to the user's dentition (step 230). Again, the whitener or bleaching agent may be any of a myriad of available products available over-the-counter or for clinical application, e.g., gels and pastes for brush-on or tray application and adhesive strips. The whitening composition is left on the user's dentition for a second period of time, which varies according to the whitening product used (step 240). The second time period may be anywhere between several minutes, several hours, or overnight. Finally, an acidic rinse composition according to the description herein may be applied to the user's dentition for a third period of time (step 250). The rinse composition operates to neutralize the basic pH environment created in the user's mouth by the enhancing composition to increase the effectiveness of the whitening composition. The rinse composition may be applied over a period of about a second or a few seconds up to approximately a few minutes to ensure effective neutralization.

It may first be noted that either of these activators, i.e., a pre-whitening activator and/or a post-whitening activator, may he used, manufactured and/or sold completely separately one from another, and indeed may be distributed apart from the whitening composition(s). In some instances, a user may use only a pre-whitening activator and then a whitening composition with or without a post-whitening activator; and in other instances, a user may use a whitening agent and a post-whitening activator without a pre-whitening activator. Even so, it may be preferred to use all three in order; namely, a pre-whitening activator, then a whitening agent or agents (see below), and finally a post whitening activator as described hereinabove. In such a case, the combination may be referred to as a three-component system (pre-whitening, whitening, and post whitening). In some other instances, the whitening composition/system itself may occur in one or two or more components as described in the co-pending U.S. patent applications Ser. Nos. 11/355,924 and 11/355,925, entitled "Whitening system capable of delivering effective whitening action" and "Foaming Compositions and Methods," respectively, both filed Feb. 15, 2006, and the overall system may then reflect the total number of components. For example, when the whitening system itself includes two components, then, a system hereof may be a four-component system; namely, a pre whitening component, whitening in two component parts, and a post-whitening component. The method of use hereof would be as described in FIG. 2 with the modification of including the mixing of the two parts of the whitening composition prior to or during application thereof to the dental surfaces, after the initial pre-whitening enhancing application and before the post-whitening enhancing application.

The above specification, examples and data provide, a complete description of the structure, process, and use of exemplary embodiments of the invention. Although various embodiments of this invention have been described above with a certain degree of particularity. or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A method of using an enhancing composition comprising
 a solvent; and
 a base compound dissolved in the solvent to form an alkaline solution;
 wherein the base compound is potassium hydroxide;
 further comprising an acid compound to reduce a pH measure of the enhancing composition to a biologically compatible level;
 wherein the acid compound comprises tartaric acid; and,
 further comprising a surfactant; the method being for oral use as a pre-treatment composition of a tooth whitening composition, the method comprising
 applying the enhancing compound to a user's dentition; and
 applying the tooth whitening composition either simultaneously with the enhancing compound or within a period thereafter.

2. The method of claim 1, wherein the step of applying further comprises using the enhancing compound to wet the surfaces of the dentition within an oral cavity containing the user's dentition.

3. The method of claim 1, wherein the step of applying further comprises one or both of swabbing and agitating the enhancing compound on the user's dentition.

4. The method of claim 1, wherein the step of applying further comprises brushing the enhancing compound on the user's dentition.

* * * * *